United States Patent [19]

Erpenbach et al.

[11] 4,308,175
[45] Dec. 29, 1981

[54] CARRIER-SUPPORTED CATALYST AND PROCESS FOR MAKING IT

[75] Inventors: Heinz Erpenbach, Cologne; Klaus Gehrmann; Herbert Joest, both of Erftstadt, all of Fed. Rep. of Germany

[73] Assignee: Hoechst Aktiengesellschaft, Frankfurt am Main, Fed. Rep. of Germany

[21] Appl. No.: 93,896

[22] Filed: Nov. 13, 1979

[30] Foreign Application Priority Data

Nov. 16, 1978 [DE] Fed. Rep. of Germany ....... 2849637

[51] Int. Cl.$^3$ .................. B01J 29/00; B01J 23/16; C07C 2/64; C07C 4/06
[52] U.S. Cl. .................................. 252/458; 252/465; 585/445
[58] Field of Search ............... 585/445, 440, 630, 660, 585/530, 502, 506; 252/454, 458, 465

[56] References Cited

U.S. PATENT DOCUMENTS

| | | | |
|---|---|---|---|
| 2,420,563 | 5/1947 | Reynolds | 585/630 |
| 3,998,721 | 12/1976 | O'Hara | 252/458 |
| 4,139,493 | 2/1979 | Mickelson | 252/458 |
| 4,192,961 | 3/1980 | Polyakov et al. | 252/458 |

FOREIGN PATENT DOCUMENTS

| | | | |
|---|---|---|---|
| 693822 | 9/1964 | Canada | 585/445 |
| 831987 | 1/1970 | Canada | 585/445 |
| 2738576 | 3/1979 | Fed. Rep. of Germany | 585/445 |
| 47-27211 | 7/1972 | Japan | 585/445 |

Primary Examiner—Gary P. Straub
Attorney, Agent, or Firm—Connolly and Hutz

[57] ABSTRACT

The invention relates to a carrier-supported catalyst comprising oxides of chromium and tungsten and at least one of the oxides of molybdenum and potassium in the atomic ratio of $Cr_1W_{0.1-0.5}Mo_{0-0.05}K_{0-0.5}$ on a porous carrier material, and to a process for making it. To this end, the process provides (a) for a dry porous carrier material to be saturated with water up to 40 to 80% of its predetermined saturation value;

(b) for the carrier material treated as under (a) to be impregnated in any sequential order, but at least once with an aqueous solution of water-soluble compounds of chromium and, if desired, potassium, and sequentially, but at least once with a separately produced aqueous solution of a water-soluble compound of tungsten and, if desired, molybdenum, the aqueous solutions being used in either case in a quantity which is at most necessary for complete saturation;

(c) for the carrier material to be dried after each impregnation over a period of 2 to 20 hours at 350 to 500 K, and (d) for the carrier material to be sintered over a period of 0.5 to 12 hours at 550 to 1000 K, in a stream of air.

The carrier-supported catalyst finds use in the production of styrene by subjecting ethylbenzene to oxidative dehydrogenation with molecular oxygen in gas phase.

3 Claims, 1 Drawing Figure

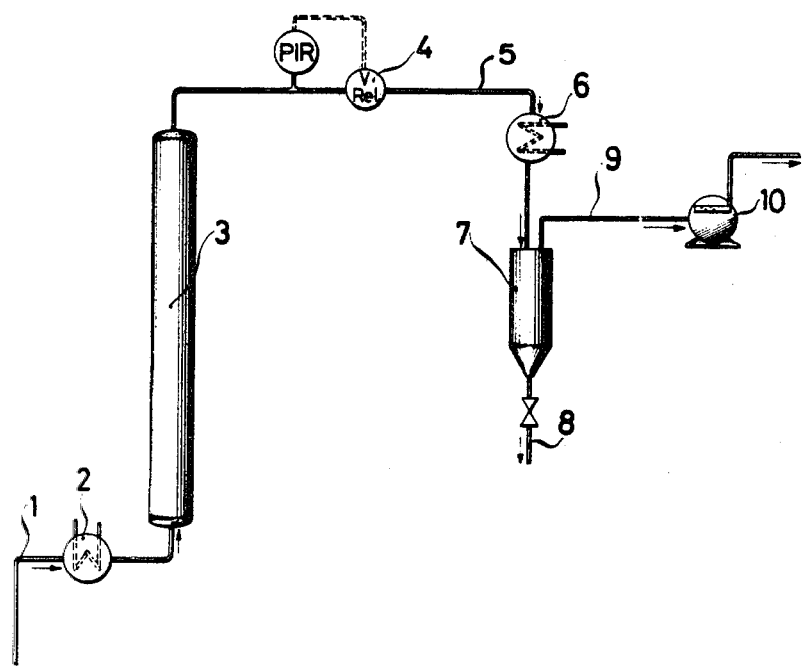

CARRIER-SUPPORTED CATALYST AND PROCESS FOR MAKING IT

The present invention relates to a carrier-supported catalyst, to a process for making it, and to its use in the production of styrene by subjecting ethylbenzene to an oxidative dehydrogenation reaction with molecular oxygen in gas phase.

Carrier-supported catalysts for use in the above reaction have already been described, e.g. in British Patent Specification No. 1,148,108, wherein ethylbenzene is subjected to oxidative dehydrogenation with air, in the presence of steam, at 350° to 600° C. and with the use of a flow bed catalyst consisting of chromium oxide and an alkali metal oxide which are deposited on a carrier. U.S. Pat. No. 3,917,732 describes a process, wherein the oxidative dehydrogenation is effected in the presence of a magnesium/nickel/pyrophosphate-catalyst and in the presence of helium, nitrogen or steam as an inert diluent. U.S. Pat. No. 3,923,916 discloses a process, wherein the oxidative dehydrogenation is carried out with the use of nickel pyrophosphate as a catalyst and helium as an inert diluent. The process described in U.S. Pat. No. 3,935,126 relates to the oxidative dehydrogenation in the presence of an alkaline earth metal/nickel/phosphate-catalyst and nitrogen or helium as an inert diluent. U.S. Pat. No. 3,957,897 describes an analogous reaction, however with the use of an alkaline earth metal pyrophosphate-catalyst and helium as an inert diluent.

Most of the catalysts described heretofore are scarcely suitable for use in the commercial production of styrene as they are required to be used together with an inert diluent, such as helium or nitrogen which in turn has to be circulated with heavy expenditure of energy, or it is necessary for the inert gases to be subjected to low cooling or scrubbing treatment whereby the recovery of styrene is naturally rendered very difficult. A more serious adverse effect encountered with the catalysts described heretofore, which incidentally should be highly selective, resides in their unsatisfactory productivity of at most 135 g of styrene per liter of catalyst per hour, determinable by gas-chromatographic analysis in smallest apparatus units only. As appears to result from the data given in British Patent Specification No. 1,148,108, the productivity is even as low as 75 g of styrene per liter of catalyst per hour, in the commercial production of styrene.

It is therfore an object of the present invention to provide a process for making oxidic carrier-supported catalysts which are free from the adverse effects described hereinabove and enable ethylbenzene to be subjected to oxidative dehydrogenation to give styrene under technically and commercially attractive conditions.

The present invention relates more particularly to a carrier-supported catalyst comprising oxides of chromium and at least one of the oxides of molybdenum and potassium, respectively, in the atomic ratio of $Cr_1W_{0.1-0.5}Mo_{0-0.05}K_{0-0.5}$, the oxides being deposited on a porous carrier material.

Preferred features of the present invention provide:
(a) for the carrier material to have a BET-surface area of 0.1 to 500 m²/g, preferably 2 to 200 m²/g;
(b) for the carrier material to be used in the form of particles with a size of 0.01 to 6 mm, preferably 0.01 to 0.2 mm, for use in a flow bed, or 3 to 6 mm for use in a fixed bed;
(c) for the catalyst to contain 2 to 30 weight % of the oxides of chromium and tungsten, molybdenum and/or potassium; and
(d) for the catalyst to contain silicic acid or aluminum oxide as the porous carrier material.

The present invention also relates to a process for making the carrier-supported catalyst which comprises:
(a) saturating a dry porous carrier material with water up to 40 to 80% of its predetermined saturation value;
(b) impregnating the carrier material treated as under (a) in any desirable sequential order, but at least once with an aqueous solution of water-soluble compounds of chromium and, if desired, potassium, and sequentially, but at least once with a separately produced aqueous solution of a water-soluble compound of tungsten and, if desired, molybdenum, the aqueous solutions being used in either case in a quantity which is at most necessary for complete saturation;
(c) drying the carrier material after each impregnation over a period of 2 to 20 hours at 350 to 500 K.; and
(d) sintering the carrier material over a period of 0.5 to 12 hours at 550 to 1000 K., preferably 600 to 900 K., in a stream of air.

A preferred feature of the present process provides for the carrier material treated as under (a) above to be impregnated at temperatures of 290 to 375 K. A further preferred feature provides for the carrier material to be impregnated continuously with partial evaporation.

The invention finally relates to the use of the present carrier-supported catalyst in the production of styrene by subjecting ethylbenzene to an oxidative dehydrogenation reaction with molecular oxygen in gas phase, and to the use of the styrene so made.

The present process permits the reaction just described to be effected at high selectivity and productivity. The terms "conversion rate, yield, selectivity and productivity" as used herein are defined as follows:

$$\text{Conversion rate (\%)} = \frac{\text{mol ethylbenzene used per hour} - \text{mol ethylbenzene recovered per hour from reaction product}}{\text{mol ethylbenzene used per hour}} \cdot 100$$

$$\text{Yield (\%)} = \frac{\text{mol styrene obtained per hour} \cdot 100}{\text{mol ethylbenzene used per hour}}$$

$$\text{Selectivity \%} = \frac{\text{yield}}{\text{conversion rate}} \cdot 100$$

$$\text{Productivity} = \frac{\text{g styrene produced}}{\text{liter catalyst per hour}}$$

In making the catalyst of this invention, it is good practice to use chromium and potassium in the form of their nitrates, oxides or hydroxides, but use can also be made of the corresponding chlorides, carbonates and organic acid salts (formates, acetates, citrates). Molybdenum and tungsten should preferably be used in the form of ammonium salts, especially ammonium heptamolybdate or ammonium paratungstate or together with potassium in the form of potassium molybdate or potassium tungstate, in solution.

In preparing the present catalyst, the $SiO_2$ or $Al_2O_3$-carrier material, which is preferably used in the form of spheroidal particles, is impregnated with water up to 40 to 80% of its absorbing power. This is done to make it possible for the dissolved catalytically active compounds, which are applied to the carrier jointly with or separately from, one another, and gradually, to concentrate substantially in the surface portions of the catalyst carrier.

With the use of the present carrier-supported catalyst, it is possible to effect the oxidative dehydrogenation of ethylbenzene to give styrene as follows:

Ethylbenzene and oxygen are used in a molar ratio of 1:0.1–1 and passed through or over the catalyst in the presence of 1 to 5 mols of steam and 0–4 mols of an inert gas, such as $N_2$ or $CO_2$ per mol of ethylbenzene, at temperatures of 550 to 1000 K. and under pressures of 1 to 5 bars, in a fixed bed, flow bed or fluidized bed.

The process of this invention will now be described with reference to the accompanying exemplary flow scheme comprising a single FIGURE of drawings.

Ethyl benzene, pure oxygen or air, steam and, if desired nitrogen or carbon dioxide, are introduced via a conduit 1 and a heat exchanger 2 into a jacketed reactor 3. Inside the heat exchanger 2, the feed mixture is preheated to 440 to 550 K. Placed in the space formed between the wall of the reactor 3 and its jacket is an electrically heatable sand or salt bath with the aid of which the reaction temperature of 550 to 1000 K., preferably 600 to 900 K., is established. The reaction pressure is maintained at 1 to 5, preferably 1 to 3 bars, by means of an automatic control valve 4. The catalyst is contacted with gaseous feed mixture at a spatial velocity of 100 to 3000, preferably 500 to 1500 $h^{-1}$ (spatial velocity=normal liters (S.T.P.) of feed mixture divided by liter of catalyst inside reactor per hour). This gives a 0.1 to 30 second, preferably 0.5 to 6 second, contact time of the feed mixture with the catalyst. The resulting reaction gases are taken from the reactor 3 through a conduit 5 and a condenser 6. In a separator 7, they are separated into liquid condensate and off-gas. The condensed reaction products are removed through a conduit 8, weighed and analyzed gas-chromatographically. The off-gas is allowed to escape from the system through a conduit 9. A gas meter 10 is used to determine the quantity of off-gas of which the composition is determined by gas-chromatography.

The following Examples illustrate the invention.

EXAMPLE 1

600 g of spheroidal $SiO_2$ particles (diameter=4–5 mm; BET-surface area=135 $m^2/g$) were placed in a rotary evaporator, impregnated first with 300 g of water up to 67% of the saturation value and then continuously with a solution of 900 g of water and 40 g of $(NH_4)_{10}W_{12}O_{41}.11H_2O$ at a temperature of 370 K. with partial evaporation of water. Next, the whole was dried for 12 hours at 390 K. and impregnated with a solution of 450 g of water, 150.3 g of $CrO_3$ and 12.74 g of KOH. After impregnation, the whole was dried for 16 hours at 400 K. and sintered for 10 hours at 720 K., in a stream of air. The resulting catalyst contained 24.6 weight % of catalytically active ingredients of the composition $CR_1W_{0.1}K_{0.15}O_{3.375}$.

EXAMPLE 2

450 g of $SiO_2$-particles (size=0.01–0.2 mm; BET-surface area=185 $m^2/g$) were placed in a kneading bag, impregnated first with 350 g of water, corresponding to 58% of the saturation value, and then with a solution of 250 g of water, 91.76 g of $CrO_3$ and 7.72 g of KOH, which was kneaded thereinto at 295 K. The whole was dried for 10 hours at 380 K. and impregnated a second time with a solution of 1.62 g of $(NH_4)_6Mo_7O_{24}.4H_2O$ in 250 g of water. The material so treated was dried for 2 hours at 400 K. and a solution of 1200 g of water and 24.77 g of $(NH_4)_{10}W_{12}O_{41}.11H_2O$ was applied thereto in two portions, the second portion being applied after an intermediary 10 h drying period. The catalyst so made was dried for 16 hours at 400 K. and sintered for 1 hour at 820 K. in a stream of air. It contained 21.2 weight % of catalytically active ingredients with the composition $Cr_1W_{0.1}Mo_{0.01}K_{0.15}O_{3.405}$.

EXAMPLE 3

552 g of $Al_2O_3$-particles (size=3–6 mm, BET-surface area=175 $m^2/g$) were placed in a rotary evaporator, impregnated first with 400 g of water, corresponding to 66% of the saturation value and then with a solution of 200 g of water, 137.4 g of $CrO_3$ and 11.44 g of KOH at 370 K. with continuous evaporation of the water. The whole was dried for 4 hours at 390 K. and a second solution of 800 g of water and 42.64 g of $(NH_4)_{10}W_{12}O_{41}.11H_2O$ was then applied thereto in two operations. Next, the whole was dried for 16 hours at 400 K. and sintered for 10 hours at 720 K. in a stream of air. The resulting catalyst contained 25 weight% of catalytically active ingredients with the composition $Cr_1W_{0.12}K_{0.15}O_{3.435}$.

EXAMPLE 4

431 g of $SiO_2$-particles (size=0.01–0.2 mm; BET-surface area=145 $m^2/g$) were placed in a bag of plastics material, impregnated therein first with 350 g of water, corresponding to 78% of the saturation value, and then with a solution of 100 g of water, 21.36 g of $CrO_3$ and 1.8 g of KOH at 295 K., which was kneaded thereinto. The whole was dried for 2 hours at 400 K. and a solution of 350 g of water and 5.77 g of $(NH_4)_{10}W_{12}O_{41}.11H_2O$ was applied thereto. Next, the whole was dried for 16 hours at 400 K. and sintered for 10 h at 670 K., in a stream of air. The resulting catalyst contained 6 weight % of catalytically active ingredients with the composition $Cr_1W_{0.1}K_{0.15}O_{3.375}$.

EXAMPLE 5

600 g of spheroidal $SiO_2$-particles (size=5 mm; BET-surface area=40 $m^2/g$) were placed in a rotary evaporator, impregnated first with 500 g of water, corresponding to 71% of the saturation value, and then continuously at 370 K. with a solution of 1200 g of water and 60 g of $(NH_4)_{10}W_{12}O_{41}.11H_2O$ with partial evaporation of the water. The whole was dried for 6 hours at 390 K. and a solution of 500 g of water and 150.3 g of $CrO_3$ was applied thereto. Next, the whole was dried again for 5 hours at 490 K. and impregnated with a solution of 200 g of water and 4 g of $(NH_4)_6Mo_7O_{24}.4H_2O$. The whole was then dried for 12 hours at 400 K. and sintered for 10 hours at 750 K. in a stream of air. The resulting catalyst containing 25.5 weight % of catalytically active ingredients with the composition $Cr_1W_{0.15}Mo_{0.015}O_{3.495}$.

EXAMPLE 6

658 g (1 liter) of the catalyst of Example 1 with the composition $Cr_1W_{0.1}K_{0.15}O_{3.375}$ on $SiO_2$ as the carrier was placed in a fixed bed reactor (capacity=1.2 liter; filling height=121 cm) and contacted therein per hour with 990 normal liters (spatial velocity=990 h$^{-1}$) of a mixture of 13.2 volume% of ethylbenzene, 30 volume % of air and 56.8 volume % of steam. 32.8% of the ethylbenzene underwent conversion under a pressure of 1.05 bars inside the reactor, at a reaction temperature of 791 K. and a contact time of 1.3 seconds. Styrene was obtained in a yield of 28%. The selectivity was 85.6% and the productivity 170 g of styrene per liter of catalyst per hour.

530 g (0.9 liter) of the catalyst of Example 2 with the composition $Cr_1W_{0.1}Mo_{0.01}K_{0.15}O_{3.405}$ on $SiO_2$ as the carrier was placed in a fluidized bed reactor (reaction space=2 liters; filling height=50 cm) and contacted therein per hour with 835 normal liters (spatial velocity=928 h$^{-1}$) of a mixture of 13 volume % of ethylbenzene, 30.4 volume % of air and 56.6 volume % of steam. 42.4% of the ethylbenzene underwent conversion under a pressure of 1.1 bars inside the reactor, at a reaction temperature of 824 K. and a contact time of 1.4 seconds. Styrene was obtained in a yield of 37.1%. The selectivity was 87.4% and the productivity 207 g of styrene per liter of catalyst per hour.

EXAMPLE 8

658 g (0.85 liter) of the catalyst of Example 3 with the composition $Cr_1W_{0.12}K_{0.15}O_{3.435}$ on $Al_2O_3$ as the carrier was placed in a fixed bed reactor and contacted therein per hour with 1070 normal liters (spatial velocity=1260 h$^{-1}$) of a mixture of 11.8 volume % of ethylbenzene, 30.9 volume % of air and 57.3 volume % of steam. 31.3% of the ethylbenzene underwent conversion under a pressure of 2.5 bars inside the reactor, at a reaction temperature of 682 K. and a contact time of 2.75 seconds. Styrene was obtained in a yield of 27.3%. The selectivity was 86.9% and the productivity 188 g of styrene per liter of catalyst per hour.

EXAMPLE 9

354 g (0.9 liter) of the catalyst of Example 4 with the composition $Cr_1W_{0.1}K_{0.15}O_{3.375}$ on $SiO_2$ as the carrier was placed in a fluidized bed reactor and contacted therein per hour with 1355 normal liters (spatial velocity=1500 h$^{-1}$) of a mixture of 15.7 volume % of ethylbenzene, 33.4 volume % of air and 50.9 volume % of steam. 29.5% of the ethylbenzene underwent conversion under a pressure of 1.1 bars inside the reactor, at a reaction temperature of 746 K. and a contact time of 0.9 second. Styrene was obtained in a yield of 25%. The selectivity was 84.6% and the productivity 300 g of styrene per liter of catalyst per hour.

EXAMPLE 10

520 g (1 liter) of the catalyst of Example 5 with the composition $Cr_1W_{0.15}Mo_{0.015}O_{3.495}$ on $SiO_2$ as the carrier was placed in a fixed bed reactor and contacted therein per hour with 1200 normal liters (spatial velocity=1200 h$^{-1}$) of a mixture of 12.5 volume % of ethylbenzene, 31 volume % of air and 56.5 volume % of steam. 37.8% of the ethylbenzene underwent conversion under a pressure of 1.2 bars inside the reactor, at a reaction temperature of 725 K. and a contact time of 1.4 seconds. Styrene was obtained in a yield of 31.3%. The selectivity was 82.9% and the productivity 218 g of styrene per liter of catalyst per hour.

We claim:

1. A process for making a carrier-supported catalyst containing 2 to 30 weight % of the oxides of chromium and tungsten and of at least one of the oxides of molybdenum and potassium in the atomic ratio of $Cr_1W_{0.1-0.5}Mo_{0-0.05}K_{0-0.5}$ on a porous carrier material selected from silicic acid or aluminum oxide, the carrier material having a BET-surface area of 2 to 200 m$^2$/g and consisting of particles with a size of 0.01 to 6 mm, which comprises:

(a) saturating the dry porous carrier material with water up to 40 to 80% of its predetermined saturation value;

(b) impregnating the carrier material treated as under (a), in any desired sequential order, but at least once with an aqueous solution of water-soluble compounds of chromium and, if desired, potassium, and separately, but at least once with a separate aqueous solution of a water-soluble compound of tungsten and, if desired, with a separate aqueous solution of a water soluble compound of molybdenum, the aqueous solutions being used in either case in a quantity which is at most necessary for complete saturation;

(c) drying the carrier material after each impregnation over a period of 2 to 20 hours at 350 to 500 K.; and (d) sintering the carrier material over a period of 0.5 to 12 hours at 550 and 1000 K., in a stream of air.

2. A process for making a carrier-supported catalyst containing 2 to 30 weight % of the oxides of chromium and tungsten and of at least one of the oxides of molybdenum and potassium in the atomic ratio of $Cr_1W_{0.1-0.5}Mo_{0-0.05}K_{0-0.5}$ on a porous carrier material selected from silicic acid or aluminum oxide, the carrier material having a BET-surface area of 2 to 200 m$^2$/g and consisting of particles with a size of 0.01 to 6 mm, which comprises:

(a) saturating the dry porous carrier material with water up to 40 to 80% of its predetermined saturation value;

(b) continuously impregnating with partial evaporation the carrier material treated as under (a), in any desired sequential order, but at least once with an aqueous solution of water-soluble compounds of chromium and, if desired, potassium, and separately, but at least once with a separately produced aqueous solution of a water-soluble compound of tungsten and, if desired, with a separate aqueous solution of a water soluble compound of molybdenum;

(c) drying the carrier material after each impregnation over a period of 2 to 20 hours at 350 to 500 K.; and (d) sintering the carrier material over a period of 0.5 to 12 hours at 550 to 1000 K., in a stream of air.

3. A process as claimed in claim 1, wherein the carrier material treated as described under (a) is impregnated as described under (b) at temperatures of 290 to 375 K.

* * * * *